United States Patent [19]

Habicht et al.

[11] Patent Number: 4,500,542
[45] Date of Patent: Feb. 19, 1985

[54] DIOXAHETEROCYCLIC COMPOUNDS

[75] Inventors: Ernst Habicht, Oberwil; Paul Zbinden, Witterswil, both of Switzerland

[73] Assignee: Ciba-Geigy Corporation, Ardsley, N.Y.

[21] Appl. No.: 550,060

[22] Filed: Nov. 8, 1983

Related U.S. Application Data

[63] Continuation of Ser. No. 369,787, Apr. 19, 1982, abandoned.

[30] Foreign Application Priority Data

Apr. 24, 1981 [CH] Switzerland .......... 2697/81

[51] Int. Cl.³ .......... A61K 31/36; A61K 31/44; C07D 401/00; C07D 317/70
[52] U.S. Cl. .......... 514/465; 544/153; 546/270; 548/530; 549/433; 260/239 B; 514/338
[58] Field of Search .......... 549/433; 424/282, 263; 546/270

[56] References Cited

U.S. PATENT DOCUMENTS 3,872,105  3/1975  Grisar et al.
4,096,267  6/1978  Cragoe, Jr. et al. .......... 424/262
4,177,285  12/1979  Cragoe, Jr. et al. .......... 424/275
4,182,764  1/1980  Cragoe, Jr. et al. .......... 424/262

OTHER PUBLICATIONS

Chem. Abstracts, 71:30377m, (1969).
Chem. Abstracts, 69:18804z, (1968), 1967-71 Subject Index.

Primary Examiner—Ethel G. Love
Attorney, Agent, or Firm—Irving N. Feit

[57] ABSTRACT

The invention relates to novel dioxaheterocyclic compounds of the formula I

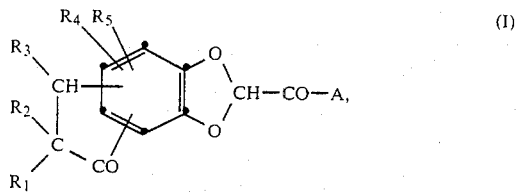

in which $R_1$ represents an unsubstituted or substituted aromatic or heteroaromatic radical or an unsubstituted or lower alkylated, mono- or bi-cyclic cycloaliphatic hydrocarbon radical or an α-branched aliphatic hydrocarbon radical, each of $R_2$ and $R_3$, independently of the other, represents hydrogen or lower alkyl, and each of $R_4$ and $R_5$, independently of the other, represents hydrogen, lower alkyl or halogen, and A represents the radical —O—$R_6$, wherein $R_6$ represents hydrogen or an unsubstituted or substituted aliphatic or araliphatic hydrocarbon radical or A represents the radical

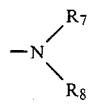

in which each of $R_7$ and $R_8$, independently of the other, represents hydrogen or lower alkyl, or $R_7$ and $R_8$ are bonded to one another and, together with the adjacent nitrogen atom, represent unsubstituted or lower alkyl-substituted tetra- to hexa-methyleneimino or 4-morpholinyl, and the divalent radical in formula I is either in the 4,5- or the 5,6-position and correspondingly $R_4$ and $R_5$ are in positions 6 and 7, or 4 and 7, respectively, of the benzodioxole skeleton, to salts of compounds of the formula I in which A represents $OR_6$ wherein $R_6$ represents hydrogen, with bases, as well as acid addition salts of compounds of the formula I in which the radical $R_1$ is of basic character, and to pharmaceutical compositions containing them. These novel substances have a diuretic activity and, in addition, a uricosuric activity, and can be administered, according to the invention, preferably in the form of corresponding pharmaceutical compositions, to mammals for the treatment of oedema and hypertension.

22 Claims, No Drawings

DIOXAHETEROCYCLIC COMPOUNDS

This application is a continuation of application Ser. No. 369,787, filed 4/19/82, now abandoned.

The invention relates to novel dioxaheterocyclic compounds with valuable pharmacological properties and pharmaceutical compositions containing them, and to the use of these novel substances and pharmaceutical compositions.

The novel compounds according to the invention correspond to the formula I

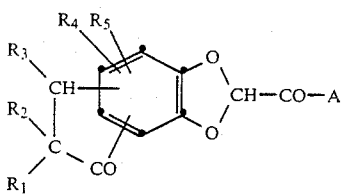

in which $R_1$ represents an unsubstituted or substituted aromatic or heteroaromatic radical or an unsubstituted or lower alkylated, mono- or bi-cyclic cycloaliphatic hydrocarbon radical or an α-branched aliphatic hydrocarbon radical, each of $R_2$ and $R_3$, independently of the other, represents hydrogen or lower alkyl, and each of $R_4$ and $R_5$, independently of the other, represents hydrogen, lower alkyl or halogen, and A represents the radical $-O-R_6$, wherein $R_6$ represents hydrogen or an unsubstituted or substituted aliphatic or araliphatic hydrocarbon radical or A represents the radical

in which each of $R_7$ and $R_8$, independently of the other, represents hydrogen or lower alkyl, or, $R_7$ and $R_8$ are bonded to one another and, together with the adjacent nitrogen atom, represent unsubstituted or lower alkyl-substituted tetra- to hexamethyleneimino or 4-morpholinyl, and the divalent radical in formula I is either in the 4,5- or the 5,6-position and correspondingly $R_4$ and $R_5$ are in positions 6 and 7, or 4 and 7, respectively, of the benzodioxole skeleton. They may be in the form of mixtures of racemates, racemates, diastereoisomeric antipode mixtures or optical antipodes. The invention relates also to salts of compounds of the formula I in which A represents $OR_6$ wherein $R_6$ represents hydrogen, with bases, as well as to acid addition salts of compounds of the formula I in which the radical $R_1$ is of basic character.

Unless indicated to the contrary, hereinbefore and hereinafter there are to be understood by lower radicals or compounds those having a maximum of 7, preferably a maximum of 4, carbon atoms.

An aromatic radical $R_1$ is especially a 1- or 2-naphthyl radical and especially a phenyl radical, A heteroaromatic radical is preferably a bicyclic or, especially, a monocyclic radical. As a corresponding monocyclic radical, $R_1$ contains especially two nitrogen atoms or preferably one nitrogen atom and/or an oxygen or sulphur atom, and is, for example, a mono- or diaza-cyclic, oxa- or thia-cyclic or oxaza- or thiaza-cyclic radical having 5 ring members, for example 1H-pyrrolyl, such as 1H-pyrrol-2-yl or -3-yl, 1H-pyrazolyl, such as 1H-pyrazol-3-yl, -4-yl or -5-yl, 1H-imidazolyl, such as 1H-imidazol-2-yl, -4-yl or -5-yl, furyl, such as 2- or 3-furyl, thienyl, such as 2- or 3-thienyl, oxazolyl, such as 2-oxazolyl, isoxazolyl, such as 3- or 5-isoxazoly, thiazolyl, such as 2- or 4-thiazolyl, or a mono- or diaza-cylic radical having 6 ring members, for example pyridyl, such as 2-, 3- or 4 -pyridyl, pyridazinyl, such as 3-pyridazinyl, pyrimidinyl, such as 2-, 4- or 5-pyrimidinyl, or 2-pyrazinyl. Corresponding bicyclic radicals $R_1$ consist, for example, of a 5-membered hetero ring of aromatic character having two nitrogen atoms or having one nitrogen atom and/or an oxygen or sulphur atoms as ring members and a fused benzene ring, or of a 6-membered hetero ring of aromatic character having two or, especially, one nitrogen atom as ring member(s) and a fused benzene ring. Accordingly, bicyclic heteroaryl is, for example, 1H-indolyl, such as 1H-indol-2-yl, -3-yl, -4-yl, -5-yl or -6-yl, 1H-indazolyl, such as 1H-indazol-3-yl, 1H-benzimidazolyl, such as 1H-benzimidazol-2-yl, -4-yl, -5-yl or -6-yl, benzofuranyl, such as 2-, 3-, 5- or 6-benzofuranyl, benzo[b]thienyl, such as benzo[b]thien-2-yl, -3-yl, -5-yl or -6-yl, benzoxazolyl, such as 2-, 4-, 5- or 6-benzoxazolyl, benzothiazoly, such as 2-, 4-, 5- or 6-benzothiazolyl, or, for example, quinolinyl, such as 2-, 4-, 5- or 6-quinolinyl, isoquinolinyl, such as 1-, 3- or 4-isoquinolinyl, quinazolinyl, such as 2-, 4- or 6-quinazolinyl, quinoxalinyl, such as 2- or 6-quinoxalinyl, or phthalazinyl, such as 1- or 6-phthalazinyl. As a substituted aromatic or heteroaromatic radical, $R_1$ is substituted one or more times, preferably a maximum of three times, for example by halogen, such as fluorine, bromine, iodine or, especially, chlorine, by lower alkyl, such as, for example, ethyl, propyl, isopropyl, butyl, isobutyl, tert.butyl or, especially, methyl, and/or by lower alkoxy, such as ethoxy, propoxy, isopropoxy, butoxy, isobutoxy and, especially, methoxy, and/or by trifluoromethyl.

Unsubstituted or lower alkylated cycloalkyl is, for example, cyclopentyl, cyclohexyl, cycloheptyl, 2-norbornyl or bicyclo[2.2.2]oct-2-yl each of which is unsubstituted or substituted one or more times, preferably a maximum of three times, by lower alkyl, especially methyl, ethyl, isopropyl and/or tert. butyl, and contains a total maximum number of 12, and preferably a total maximum number of 10, carbon atoms.

α-branched lower alkyl $R_1$ is, for example, isopropyl, sec. butyl, tert. butyl, 1-ethylpropyl, tert. pentyl, 1-ethylbutyl or 1-propylbutyl.

$R_2$ and $R_3$ as lower alkyl are, for example, ethyl, propyl, butyl or isobutyl and, especially, methyl; $R_3$ especially, however, can also be, for example, isopropyl or tert. butyl.

$R_4$ and $R_5$ are as lower alkyl, for example, one of the afore-mentioned radicals, especially methyl, and as halogen fluorine, bromine, iodine or, especially, chlorine. In the radical A, $R_6$ as an unsubstituted or substituted aliphatic or araliphatic hydrocarbon radical is, for example, alkyl having a maximum of 12 carbon atoms, especially lower alkyl, also 2- or 3-lower alkenyl or 2-lower alkynyl, lower alkoxy-lower alkyl, halogenated lower alkyl, such as geminal polyhalo-lower alkyl, or, for example, phenyl-lower alkyl or cinnamyl in which the phenyl radical may be substituted, for example, in the same manner as a phenyl radical $R_1$. Alkyl $R_6$ is, for example, propyl, isopropyl, butyl, isobutyl, pentyl, isopentyl, neopentyl, hexyl, heptyl, octyl, nonyl, decyl, dodecyl and, especially, methyl or ethyl; lower alkenyl $R_6$ is, for example, allyl, 1- or 2-methallyl, 2-butenyl or 3-butenyl; lower alkynyl is, for example, 2-propynyl; lower alkoxy-lower alkyl is especially 2- or 3-lower alkoxy-lower alkyl, such as, for example, 2-methoxy-, 2-ethoxy-, 2-isopropoxy- or 2-butoxy-ethyl, 2- or 3-methoxypropyl, 2- or 3-ethoxypropyl, also 3- or 4-methoxybutyl or 3- or 4-ethoxybutyl, and halogenated lower alkyl is especially geminally polyhalogenated lower alkyl, such as 2,2,2-trifluoro- or 2,2,2-trichloroethyl. Phenyl-lower alkyl $R_6$ is, for example, benzyl, 2-phenylethyl, 2- or 3-phenylpropyl or 2-, 3- or 4-phenylbutyl.

Salts of the novel compounds are especially salts of compounds of the general formula I in which A represents $OR_6$ wherein $R_6$ represents hydrogen, with bases, especially pharmaceutically acceptable salts of such compounds with bases. There come into consideration as such salts with bases, for example alkali metal or alkaline earth metal salts, such as sodium, potassium, calcium or magnesium salts, and also ammonium salts with ammonia or organic amines, such as mono- or di-lower alkylamines, for example methylamine, ethylamine, dimethylamine or diethylamine, or mono-, di- or tri-(hydroxyalkyl)amines, for example 2-aminoethanol, 2-(dimethylamino)-ethanol, 2-(diethylamino)-ethanol, 2,2'-iminodiethanol or 2,2',2''-nitrilotriethanol.

As acid addition salts, especially pharmaceutically acceptable acid addition salts, of compounds of the general formula I in which $R_1$ is of basic character, there come into consideration, for example, those with suitable inorganic acids, such as hydrohalic acids, for example hydrochloric acid or hydrobromic acid, also nitric acid, sulphuric acid or phosphoric acid, or with suitable organic acids, such as carboxylic acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicyclic acid, 4-aminosalicyclic acid, 2-phenoxybenzoic acid, 2-acetoxybenzoic acid, embonic acid, nicotinic acid or isonicotinic acid, or organic sulphonic acids, such as lower alkanesulphonic acids optionally containing hydroxy, for example methanesulphonic acid, ethanesulphonic acid, 2-hydroxyethanesulphonic acid or ethane-1,2-disulphonic acid, or arenesulphonic acids, for example benzenesulphonic acid, 4-methylbenzenesulphonic acid or naphthalene-2-sulphonic acid, or other acidic substances, such as ascorbic acid.

The novel dioxaheterocyclic compounds of the general formula I and their salts possess valuable pharmacological properties. They have, in particular, a diuretic and naturetic action, in rats in a dosage range of from 10 to 100 mg/kg per os and in dogs in a dosage range of from 1 to 20 mg/kg per os, as can be ascertained by collecting the urine over a period of 3 hours after administration (rats) or hourly for 5 hours after administration (dogs) and determining the volume of urine and the sodium, potassium and chlorine ions. The potassium excretion is not increased until the higher doses and is then increased to a lesser extent than is the excretion of sodium; attention is also drawn to the good tolerability of the compounds of the general formula I. For example, by administering 10 mg/kg per os of the sodium salt of 7,8-dihydro-5,7-dimethyl-6-oxo-7-phenyl-6H-indeno[4,5-d]-1,3-dioxole-2-carboxylic acid itself melting at 161°–163° and 10 mg/kg per os of the sodium salt of 7,8-dihydro-5,7-dimethyl-7-(2-fluorophenyl)-6-oxo-6H-indeno[4,5-d]-1,3-dioxole-2-carboxylic acid to rats (6 and 3 animals respectively per dose), in comparison with untreated control animals, the excretion of sodium ions is increased by a factor of 5 and 6, respectively, of potassium ions by a factor of 3 and 1.8, respectively, and of chlorine ions by a factor of 8 and 8.5, respectively. The administration to dogs of 1 and 5 mg/kg per os of the first-mentioned sodium salt (3 animals per dose) increases the average excretion per minute for the first 5 hours after administration by comparison with the average excretion per minute during the last hour before administration, in the case of the sodium ions by a factor of 17 and 39, respectively, in the case of the potassium ions by a factor of 1.5 and 2.5, respectively, in the case of the chlorine ions by a factor of 12 and 29, respectively, and as regards the volume of urine by a factor of 2 and 8, respectively. Also, compounds of the general formula I, such as, for example, the first of the afore-mentioned sodium salts or the sodium salt of 6,7-dihydro-6-methyl-5-oxo-6-phenyl-5H-indeno[5,6-d]-1,3-dioxole-2-carboxylic acid, possess a uricosuric activity, as may be demonstrated, for example, by tests on Cebus apes (*Cebus apella*). In these test the test animals, narcoticised with pentabarbital, are given, by intravenous infusion, polyfructosane in Ringer solution and the test substance in the form of an aqueous solution is injected intravenously in increasing doses. Urine is collected for 2 to 4 10-minute periods before the first administration of test substance and after each dose of test substance, and an arterial blood sample is taken before the first and after the last collection period. The uric acid and polyfructosane clearance is calculated from the plasma and urine concentration and finally the fractional excretion of uric acid ($FE_{UR}$) is ascertained as a quotient of uric acid clearance and glomerular filtration rate. In this test, compounds of the general formula I exhibit activity in a dosage range of from 2 to 10 mg/kg i.v.; for example the administration of 10 mg/kg of the first or the third of the afore-mentioned sodium salts doubles the fractional excretion of uric acid. Accordingly, the compounds of the general formula I and their pharmaceutically acceptable salts can be used as potassium-neutral diuretics having supplementary uricosuric action, for example for the treatment of oedema and hypertension.

The invention relates especially to compounds of the general formula I in which $R_1$ represents phenyl or pyridyl each of which is unsubstituted or substituted by lower alkyl, lower alkoxy or halogen, $R_2$ represents primary lower alkyl, each of $R_3$ and $R_4$ independently of the other, represents hydrogen or lower alkyl, $R_5$ represents hydrogen and A has the meaning given under formula I but represents especially $OR_6$ in which $R_6$ represents hydrogen or lower alkyl, and the divalent radical in formula I is either in the 4,5- or the 5,6-position of the benzodioxole skeleton, in the form of mixtures of racemates, diastereoisomeric antipode mixtures or, especially, in the form of racemates or optical antipodes, and to the salts of those compounds in which A represents $OR_6$ wherein $R_6$ represents hydrogen, with bases.

The invention relates more especially to compounds of the general formula I in which $R_1$ represents phenyl or pyridyl each of each is unsubstituted or substituted by lower alkyl, lower alkoxy or halogen, $R_2$ represents primary lower alkyl, $R_3$ represents hydrogen or lower alkyl, $R_5$ represents hydrogen and A represents $OR_6$ wherein $R_6$ represents hydrogen or lower alkyl, and $R_4$ represents lower alkyl bonded in the 5-position of the tricyclic compound and at the same time the divalent radical in formula I is in the 4,5-position of the benzodioxole skeleton, or R4 represents hydrogen and at the same time the divalent radical in formula I is in the 5,6-position of the benzodioxole skeleton, in the form of mixtures of racemates, diastereoisomeric antipode mixtures or, especially, in the form of racemates or optical antipodes, and to the pharmaceutically acceptable salts of those compounds in which A represents $OR_6$ wherein $R_6$ represent hydrogen, with bases.

The invention relates above all to compounds of the general formula I in which $R_1$ represents phenyl that is unsubstituted or substituted by lower alkyl, lower alkoxy or halogen, $R_2$ represents primary lower alkyl, each of $R_3$ and $R_5$ represents hydrogen and A represents $OR_6$ wherein $R_6$ represents hydrogen or lower alkyl, and $R_4$ represents lower alkyl bonded in the 5-position of the tricyclic compound and at the same time the divalent radical in formula I is in the 4,5-position of the benzodioxole skeleton, or $R_4$ represents hydrogen and at the same time the divalent radical in formula I is in the 5,6-position of the benzodioxole skeleton, in the form of mixtures of racemates, diastereoisomeric antipode mixtures or, especially, in the form of racemates or optical antipodes, and to the pharmaceutically acceptable salts of those compounds in which A represents $OR_6$ wherein $R_6$ represents hydrogen, with bases.

The invention relates first and foremost to compounds of the general formula I in which $R_1$ represents phenyl that is substituted by lower alkyl, lower alkoxy or halogen, especially fluorine, or, especially, unsubstituted phenyl, $R_2$ represents primary lower alkyl, especially methyl, each of $R_3$ and $R_5$ represents hydrogen and A represents $OR_6$ wherein $R_6$ represents hydrogen or lower alkyl, and $R_4$ represents methyl bonded in the 5-position of the tricyclic compound and at the same time the divalent radical in formula I is in the 4,5-position of the benzodioxole skeleton, or $R_4$ represents hydrogen and at the same time the divalent radical in formula I is in the 5,6-position of the benzodioxole skeleton, and to the pharmaceutically acceptable salts of those compounds in which A represents $OR_6$ wherein $R_6$ represents hydrogen, with bases; such as to the carboxylic acids forming the basis of the three afore-mentioned sodium salts and to their pharmaceutically acceptable salts with bases.

The novel compounds of the general formula I and salts of such compounds are produced in a manner known per se, by (a) reacting a compound of the general formula II

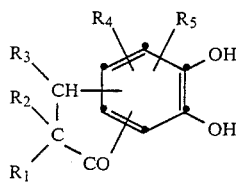

in which $R_1$, $R_2$, $R_3$, $R_4$ and $R_5$ have the meanings given under formula I, or a salt thereof, with a compound of the general formula III

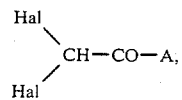

in which Hal represents halogen and A has the meaning given under formula I, or with a salt of such a compound in which A represents $OR_6$ wherein $R_6$ represents hydrogen, or (b) in a compound of the general formula

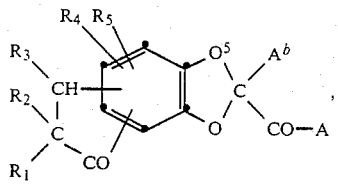

in which $A^b$ represents carboxy, lower alkoxycarbonyl or acetyl and $R_1$, $R_2$, $R_3$, $R_4$, $R_5$ and A have the meanings given under formula I, replacing the radical $A^b$ by hydrogen, or (c) to produce a compound of the general formula I in which A represents $OR_6$ wherein $R_6$ represents hydrogen, and $R_1$, $R_2$, $R_3$, $R_4$ and $R_5$ have the meanings given under formula I, or a salt of this compound, in a compound of the general formula V

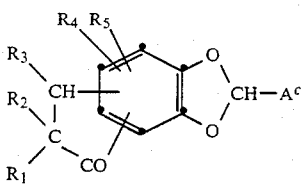

in which $A^c$ represents a group that can be converted into the carboxy group and $R_1$, $R_2$, $R_3$, $R_4$ and $R_5$ have the meanings given under formula I, converting the group $A^c$ into the carboxy group in free or salt form, or (d) to produce a compound of the general formula I in which A has the meaning given under formula I with the exception of a radical $OR_6$ wherein $R_6$ represents hydrogen, and $R_1$, $R_2$, $R_3$, $R_4$ and $R_5$ have the meanings given under formula I, in a compound of the general formula VI

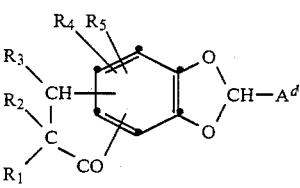

in which $A^d$ represents a radical that can be converted into a radical $—CO—A_1$ in which $A_1$ has the meaning given for A under formula I with the exception of a radical $Or_6$ wherein $R_6$ represents hydrogen, and $R_1$, $R_2$, $R_3$, $R_4$ and $R_5$ have the meanings given under formula I, converting the radical $A^d$ into the radical $—CO—A_1$, and, if desired, converting a resulting compound of the general formula I in a manner known per se into a different compound of the general formula I, and/or separating a compound of the general formula I obtained in the form of a mixture of racemates into the racemates, and/or resolving a compound of the general formula I obtained in the form of a racemate or diastereoisomeric antipode mixture into the optical antipodes, and/or converting a resulting compound of the general formula I in which A represents $OR_6$ wherein $R_6$ represents hydrogen into a salt with a base, or freeing such a compound from a resulting salt, or converting a resulting compound of the general formula I of basic character into an acid addition salt or freeing such a compound from a resulting salt.

In the starting materials of the general formula III, Hal is preferably chlorine or bromine, but can alternatively be fluorine or iodine, it also being possible for two different halogen atoms to be present. The reactions according to process a) are preferably carried out in organic solvents that are inert under the reaction conditions, for example in ethereal solvents, such as, for example, dibutyl ether, 1,2-dimethoxyethane, diethylene gylcol dimethyl ether, tetrahydrofuran or dioxan; alcoholic solvents, such as, for example, methanol, ethanol, isopropanol, butanol, 2-methoxyethanol or 2-ethoxyethanol; or amide-type solvents, such as, for example, dimethylformamide or N,N,N′,N′,N″,N″-hexamethylphosphoric acid triamide; or in hdrocarbons, such as, for example, petroleum ether, cyclohexane, benzene or toluene, Reactions with free compounds of the general formula II and also with free haloacetic acids of the general formula III are preferably carried out in the presence of basic substances. As such basic substances there may be used, for example, organic or inorganic derivatives of alkali metals or alkaline earth metals; as organic derivatives, there may be used, for example, alkali metal or alkaline earth metal alkoxides, such as sodium or lithium methoxide, ethoxide, n-butoxide or tert. butoxide, or barium methoxide, and as inorganic derivatives, for example, corresponding hydroxides, such as sodium, potassium or calcium hydroxide, or carbonates, such as, for example, sodium or potassium carbonate. Especially carbonates can be used in relatively large excess, for example up to a five-fold excess. When using carbonates, also other organic solvents, such as lower alkanones, for example acetone or 2-butanone, may come into consideration as being sufficiently inert. As salts of compounds of the general formula II and of the optionally used dihaloacetic acids falling within the scope of the general formula III there are suitable, for example, corresponding alkali metal salts or alkaline earth metal salts. The reaction temperatures lie, for example, between room temperature and approximately 150° C., and preferably between approximately 70° and 120° C.

The starting materials of the general formula II are for their part novel compounds and the materials can be produced, for example, as follows: First of all veratrole, which, following the definition for $R_4$ and $R_5$, may be substituted, is condensed according to the Friedel Crafts method with an acetyl halide substituted by aryl or heteroaryl $R_1$, for example by means of aluminium chloride in 1,2-dichloroethane at room temperature, to form the corresponding 1-(vic-dimethoxyphenyl)-2-$R_1$-1-ethanone which, following the meaning of $R_4$ and $R_5$, is optionally substituted, from which group of substances a few examples, such as 1-(3,4-dimethoxyphenyl)-2-phenyl-1-ethanone (3,4-dimethoxy-deoxybenzoin) [cf. S. F. Dyke et al., Tetrahedron 31, 1219-1222 (1975)] are known. A lower alkylidene radical is introduced into the 2-position of the resulting ethanones, for example by a modification of the Mannich reaction; for example for the production of precursors for end products in which the radical $R_3$ is hydrogen the methylene radical is introduced by reaction with bis-(dimethylamino)methane in the presence of acetic anhydride. Especially for the production of homologues, that is to say compounds with a different lower alkylidene radical, for example an ethylidene radical, in the same position, there come into consideration, for example, also the condensation of veratrole optionally substituted as defined with a 2-$R_1$-2-lower alkenoyl chloride, for example the known 2-phenylcrotonoyl chloride, as well as other processes known per se for the production of deoxybenzoins. The resulting 1-(vicdimethoxyphenyl)-2-$R_1$-2-propen-1-ones, optionally substituted according to $R_3$, $R_4$ and $R_5$, are then cyclised by means of a strong mineral acid, for example polyphosphoric acid, to form the corresponding 2,3-dihydro-5,6-(or 4,5)-dimethoxy-2-$R_1$-1H-inden-1-ones. There is then, if desired, introduced into the 2-position thereof, in a manner known per se, lower alkyl $R_2$, for example by reaction with a lower alkyl halide, such as methyl iodide, in a two-phase system comprising a concentrated aqueous solution of tetrabutylammonium hydroxide or bromide and an inert organic solvent, for example methylene chloride. Finally, starting materials of the general formula II are obtained by cleaving the two methoxy groups in a manner known per se, for example by heating with 48% strength hydrobromic acid in anhydrous acetic acid, or by heating with pyridine-hydrochloride. Some starting materials of the general formula III are known and others can be produced analogously to the known compounds.

To carry out process (b), for example a starting material of the general formula IV in which $A^b$ represents carboxy and A as well as $R_1$, $R_2$, $R_3$, $R_4$ and $R_5$ have the meanings given under formula I is heated in the presence or absence of a catalyst, for example copper powder, and/or in the presence or absence of a solvent or diluent, such as, for example, o-dichlorobenzene or 1,2,3,4-tetrahydronaphthalene, until at least an approximately equimolar amount of carbon dioxide is freed. Starting materials of the general formula IV in which $A^b$ represents carboxy and A represents $OR_6$ wherein $R_6$ represents hydrogen are produced, for example, by hydrolysis of corresponding compounds in which A represents $OR_6$ wherein $R_6$ represents lower alkyl and the substituent in the corresponding position to $A^b$ is lower alkoxycarbonyl or cyano, in acidic or alkaline medium, for example by heating with a strong mineral acid in aqueous or aqueous-organic, for example aqueous-lower alkanolic, medium, or with at least twice the molar amount of an alkali metal hydroxide, especially sodium or potassium hydroxide, for example in a lower alkanol, such as methanol, ethanol, isopropanol or n-butanol, or in a lower alkanediol or monoalkyl ether of the same, for example ethylene glycol, 2-methoxyethanol or 2-ethoxyethanol, water in a volume ratio of water to solvent of about 1:10 to 2:1 optionally being added. There can also be used as reaction medium water or, for example, a mixture of water with water-soluble, ethereal solvents, such as dioxan or tetrahydrofuran.

If the hydrolysis is carried out in a water-containing mineral acid, the decarboxylation according to the process can be carried out subsequently, that is to say, in the same medium and operation.

Starting materials of the general formula IV in which $A^b$ represents carboxy and A represents a radical corresponding to the definition under formula I with the exception of a radical $OR_6$ in which $R_6$ represents hydrogen, can be produced, for example, by analogous hydrolysis in alkaline medium of corresponding compounds in which the radical $A^b$ is lower alkoxycarbonyl using an approximately equimolar amount of an alkali metal hydroxide instead of at least twice the molar amount. Another possible method of producing such starting materials of the general formula IV is the hydrogenolysis of corresponding compounds which contain benzyloxycarbonyl in the $A^b$ position.

The dealkoxycarbonylation or deacetylation of corresponding starting materials of the general formula IV, that is those in which $A^b$ represents lower alkoxycarbonyl or acetyl and A represents any of radicals according to the given definition with the exception of a radical $OR_6$ in which $R_6$ represents hydrogen, is carried out, for example, by reaction with an approximately equimolar amount of an alkali metal lower alkoxide in an anhydrous lower alkanol, and if A represents $OR_6$ wherein $R_6$ represents lower alkyl, it is preferable to select the same lower alkanol, for example methanol, ethanol or n-butanol, both as component of the starting ester and of the lower alkoxide and as reaction medium. It is, however, also possible, to carry out a transesterification by using as reaction medium a relatively high boiling alkanol that is not the same as the lower alkanol present as ester component and distilling off a portion thereof simultaneously with the reaction according to the definition, or to allow only for a partial transesterification if the ester of the general formula I produced as reaction product is not to be used directly as active ingredient but is to be hydrolysed to form the corresponding acid. Further, there can be used as reaction medium, instead of a lower alkanol, for example also an inert organic solvent, such as, for example, benzene or toluene. The reaction according to the definition is carried out at room temperature or elevated temperature, for example at the boiling temperature of the reaction medium used. If desired, the resulting ester of the general formula I, as already mentioned in connection with the transesterification, can be hydrolysed to the corresponding acid in the same operation if water is added to the reaction medium.

The starting materials of the general formula IV in which $A^b$ represents lower alkoxycarbonyl or acetyl, and the already mentioned precursors for compounds of the general formula IV containing carboxy as radical $A^b$ that contain lower alkoxycarbonyl or cyano in the $A^b$ position, can be produced analogously to process (a) by reacting, in the presence of a base, compounds of the general formula II with geminal dihalo compounds that differ from those of the general formula III in having lower alkoxycarbonyl, acetyl or cyano instead of the hydrogen atom positioned adjacent to two halogen atoms.

In the manufacture of compounds of the general formula I in which A represents the radical $OR_6$ wherein $R_6$ represents hydrogen, according to process (c) the conversion of a group $A^c$ into the carboxy group can be carried out in a manner known per se, especially by hydrolysis in alkaline or acidic medium, it also being possible in the former case for a salt to be formed directly. Starting materials for the hydrolysis are primarily those compounds of the general formula I in which A is not a radical $OR_6$ in which $R_6$ represents hydrogen, especially those that can readily be hydrolysed, such as, for example, the lower alkyl esters, but also other functional derivatives of the carboxylic acids desired as end products, such as, for example, nitriles and imido esters, especially imido-lower alkyl esters, of carboxylic acids falling within the scope of the general formula I. The hydrolysis is carried out, for example, in lower alkanolic or aqueous-lower alkanolic alkali hydroxide solutions at room temperature up to approximately 100° C. or the boiling temperature of the reaction medium. Lower alkyl esters, such as methyl or ethyl esters, and other readily cleavable esters of carboxylic acids falling within the scope of the general formula I can be hydrolysed under even milder conditions, for example in the presence of potassium or sodium carbonate at room temperature or, if necessary, at a slightly elevated temperature of, for example, 40° C., in an aqueous-organic medium, for example by adding water to the reaction mixture obtained in the reaction according to (a) in a water-miscible solvent, such as, for example, 1,2-dimethoxyethane. From the initially obtained alkali metal salt solutions of the carboxylic acids falling within the scope of the general formula I, the corresponding pure alkali metal salt can either be obtained directly by concentration and filtration, or complete evaporation of the solvent and recrystallisation, or first of all the carboxylic acid can be freed, then purified, for example, by recrystallisation and, if desired, converted again into a salt with a suitable inorganic or organic base. Functional derivatives of the carboxylic acids falling within the scope of the general formula I may furthermore also be converted into the free carboxylic acids of the general formula I in acidic medium, for example by heating in a sulphuric acid diluted with water, for example 60-70% strength sulphuric acid, or in lower alkanolic-aqueous hydrochloric acid.

The required functional derivatives of carboxylic acids, that is to say, compounds of the general formula V which fall within the scope of the general formula I, are produced, for example, according to process (a) or (b) and other functional derivatives, such as, for example, nitriles, are produced analogously to these processes.

Starting materials of the general formula VI are, according to the nature of the radical $A^d$ they contain, for example carboxylic acids that also fall within the scope of the general formula I, further carboxylic acid halides or anhydrides, especially mixed anhydrides, activated esters, for example cyanomethyl esters, and also lower alkyl esters, which can be reacted, optionally in the presence of condensation agents, with hydroxy compounds of the general formula VII

$R_6$-OH         (VII), or ammonia or amines of the general formula VIII

$HN\begin{smallmatrix}R_7\\R_8\end{smallmatrix}$         (VIII)

in which formulae $R_6$, and $R_7$ and $R_8$, respectively, have the meanings given under formula I, or salts, especially alkali metal or alkaline earth metal salts, of the free carboxylic acids, which can be reacted with reactive esters of hydroxy compounds of the general formula VII, such as halides or organic sulphonic acid esters, for example lower alkanesulphonic acid or arenesulphonic acid esters, such as methanesulphonic acid or p-toluenesulphonic acid esters, or alternatively with carbamic acid halides, especially chlorides, derived from amines of the general formula VIII in which the radicals $R_7$ and $R_8$ are other than hydrogen; and also, for example, the imido esters, especially imido-lower alkyl esters, or nitriles, that can be hydrolysed to form esters, especially lower alkyl esters, and to form unsubstituted amides, respectively. Free carboxylic acids can be reacted, for example, also with diazo-lower alkanes to form lower alkyl esters, or with isocyanates that are derived from primary amines falling within the scope of the general formula VI, to form N-mono-substituted amides.

The reactions of free carboxylic acids with hydroxy compounds of the general formula VII are carried out advantageously in the presence of an acidic water-removing catalyst, such as a protonic acid, for example hydrochloric or hydrobromic acid, sulphuric acid, phosphoric acid or boric acid, benzenesulphonic or toluenesulphonic acid, or a Lewis acid, for example boron trifluoride etherate, in an excess of the hydroxy compound used and/or in an inert solvent, for example in a hydrocarbon of the benzene series, such as benzene or toluene, a halogenated hydrocarbon, such as chloroform, methylene chloride or chlorobenzene, or in an ethereal solvent, such as tetrahydrofuran, if necessary with distillative, for example azeotropic, removal of the water freed during the reaction. Further, the reactions can also be carried out in the presence of other water-binding condensation agents, for example carbodiimides substituted by hydrocarbon radicals, such as N,N'-diethyl-, N,N'-dicyclohexyl- or N-ethyl-N'-(3-dimethylaminopropyl)-carbodiimide, in inert organic solvents, for example those mentioned above. Halides and mixed anhydrides are reacted, for example, in the presence of acid-binding agents, for example organic, especially tertiary, nitrogen bases, such as, for example, triethylamine, ethyl diisopropylamine or pyridine, or alternatively inorganic bases, for example alkali metal or alkaline earth metal hydroxides or carbonates, such as sodium, potassium or calcium hydroxide or carbonate, in inert organic solvents, for example those mentioned above, and, if necessary, while heating. The reactions of reactive esters of carboxylic acids of the general formula I, for example the cyanomethyl esters, with hydroxy compounds of the general formula VII are carried out, for example, in a solvent that is inert towards the reactants, for example in a hydrocarbon, such as toluene or xylene, an ethereal solvent, such as tetrahydrofuran or dioxan, or, alternatively, at moderate temperatures, in an ester, such as ethyl acetate, in a temperature range of from approximately 0° C. to approximately 120° C., preferably at room temperature to approximately 60° C. For the transesterification reactions of lower alkyl esters of carboxylic acids of the general formula I there are preferably used hydroxy compounds of the general formula VII having a boiling point that is clearly above that of the esterified lower alkanol, and the reaction is carried out, for example, in an excess of the hydroxy compound and/or in an inert organic solvent, preferably one that likewise has a boiling point clearly above that of the lower alkanol, preferably in the presence of a catalyst, for example an alkali metal lower alkoxide, such as sodium or potassium methoxide or ethoxide, at elevated temperature and, preferably, with removal by distillation of the lower alkanol that is freed. The hydrolysis of imido esters, especially imido-lower alkyl esters, of carboxylic acids of the general formula I is carried out, for example, by means of a water-containing mineral acid, such as hydrochloric or sulphuric acid, and, for example, imido ester hydrochlorides obtained by the addition of hydrogen chloride to nitriles and reaction with anhydrous hydroxy compounds of the general formula VII, especially lower alkanols, can, after the addition of water, by hydrolysed directly to the corresponding esters, or, for example, the corresponding ester of the general formula I can also be obtained from a mixture of nitrile, hydroxy compound and sulphuric acid of suitable water content, without isolation of the imido ester formed in situ.

The reaction of free carboxylic acids of the general formula I with compounds of the general formula VIII is carried out, for example, in the presence of the above-mentioned water-binding agents and in the inert organic solvents mentioned above, but it is also possible to convert the ammonium salts initially formed from the free carboxylic acids and the compounds of the general formula VIII into amides of the general formula I by heating, optionally in a suitable organic solvent of medium or higher boiling point, such as, for example, xylene, chlorobenzene or 1,2,3,4-tetrahydronaphthalene, and by distillative, optionally azeotropic, removal of the water freed during the reaction.

There come into consideration as reactive functional derivatives of carboxylic acids of the general formula I for the reaction with compounds of the general formula VIII and as associated condensation agents and solvents substantially the same derivatives, condensation agents and solvents as those mentioned above for reactions with hydroxy compounds of the general formula VII, except that as acid-binding agents and optionally as the only reaction medium, it is possible to use instead of other bases, i.e. tertiary organic bases, also an excess of the compound of the general formula VIII to be reacted. The partial hydrolysis of the corresponding nitriles mentioned as a further possibility of forming N-unsubstituted amides can be carried out, for example, by means of water-containing mineral acids, such as hydrochloric acid or dilute sulphuric acid, at room temperature or at moderately elevated temperature.

The free carboxylic acid covered by the general formula I that are required as starting materials for process (d), can be produced according to process (a), (b) and/or (c), and their reactive functional derivatives can be produced in a manner known per se, for example from the free carboxylic acids.

Resulting salt-forming compounds of the formula I can be converted into salts in a manner known per se; for example compounds with hydroxy as radical A can be converted with corresponding bases, such as, for example, alkali metal hydroxides, into salts with bases, or compounds of basic character can be converted into their acid addition salts. Preferably pharmaceutically acceptable salts are produced.

Resulting salts can be converted into the free compounds in a manner known per se, for example by treatment with an acidic reagent, such as a mineral acid, or with a base, for example an alkali metal hydroxide solution, such as sodium hydroxide solution.

The compounds, including their salts, can also be obtained in the form of their hydrates, or their crystals can include the solvent used for crystallisation.

Owing to the close relationship between the novel compounds of the general formula I in which A represents hydroxy, in free form and in the form of their salts with bases, as well as between such compounds in which the radical $R_1$ is of basic character, in free form and in the form of acid addition salts, hereinbefore and hereinafter there are to be understood by the free compounds and their salts also the corresponding salts and free compounds, respectively, where appropriate with regard to meaning and purpose.

The novel compounds can, depending on the number of centres of asymmetry, which amounts to at least 2, and on the choice of starting materials, processes and methods of operation, be obtained in the form of mixtures of two or more racemates, as pure racemates, diastereoisomeric antipode mixtures or as pure optical antipodes.

Resulting mixtures of racemates can be separated into the pure racemates or diastereoisomers in known manner on the basis of the physico-chemical differences between the components, for example by chromatography and/or fractional crystallisation. Owing to the good crystallisability it is generally easily possible to obtain one of the two racemates in the form of a uniform crystallisate and, if desired, to isolate the other racemate from the mother liquor. Resulting racemates can be resolved into the optical antipodes according to known methods, for example by recrystallisation from an optically active solvent, by means of microorganisms or by reaction of an acidic end product of the general formula I with an optically active base that forms salts with the racemic acid, such as, for example, (+)-dehydroabiethylamine or (+)- or (−)-ephedrine, or by reaction of a basic end product of the general formula I with an optically active acid, such as, for example, (+)- or (−)-di-O,O'-(p-toluoyl)-tartaric acid and separation of the salts formed in this manner, for example on the basis of their different solubilities, into the diastereoisomers, from which the antipodes can be freed by the action of suitable agents. Advantageously, the more active of the two antipodes is isolated.

The invention relates also to those forms of the process according to which a compound obtainable as intermediate at any stage of the process is used as starting material and the remaining process steps are carried out, or a starting material is used in the form of a salt and/or racemate or antipode or, especially, is formed under the reaction conditions. For example, in process (a) an optical antipode of a compound of the general formula II may be used and there may thus be obtained as direct reaction product, instead of a mixture of two diastereoisomeric racemates, a mixture of two diastereoisomeric optical antipodes that do not correspond to one another, that is to say a diastereoisomeric antipode mixture, which can be resolved either by means of customary physical methods or analogously to racemic antipode mixtures, that is by conversion into salts, for example those with organic bases, such as those already mentioned, or into other derivatives of optically active compounds, for example esters with (+)- or (−)-menthol.

In the processes of the present invention there are preferably used as starting materials those that result in the compounds described at the beginning as being especially valuable. The present invention relates also to novel starting materials and processes for their manufacture.

The invention further relates to pharmaceutical compositions that contain compounds of the general formula I as active ingredients, and to processes for their manufacture.

The pharmaceutical compositions according to the invention are those for enteral, such as oral or rectal, and for parenteral administration to warm-blooded animals. The dosage of the active ingredient, which is administered alone or together with the customary carriers and adjuncts, depends on the species of warm-blooded animal, the age and the individual condition as well as on the mode of administration. The daily doses vary between 0.3 and 30 mg/kg for mammals and, for those weighing approximately 70 kg, depending on the individual condition and age, lie preferably between 20 and 750 mg, especially between 50 and 500 mg. Corresponding oral forms of unit doses, for example dragées or tablets or capsules, contain preferably from 10 to 250 mg., especially from 25 to 150 mg, of an active ingredient according to the invention, that is to say a compound of the general formula I or a pharmaceutically acceptable salt of a compound of the general formula I capable of salt formation together with pharmaceutical carriers.

The pharmaceutical compositions of the present invention are produced in a manner known per se, for example by means of conventional mixing, granulating, confectioning, dissolving or lyophilising processes. Thus, pharmaceutical compositions for oral use can be obtained by combining the active ingredient with solid carriers, optionally granulating a resulting mixture, and processing the mixture or granulate, if desired or necessary after the addition of suitable adjuncts, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes, using, for example, corn, wheat, rice or potato starch, gelatin, tragacanth, methylcellulose and/or polyvinylpyrrolidone and/or, if desired, disintegrators, such as the above-mentioned starches, also carboxymethyl starch, crosslinked polyvinylpyrrolidone, agar, alginic acid or a salt thereof, such as sodium alginate. Adjuncts are especially flowregulating and lubricating agents, for example silica, talc, stearic acid or salts thereof, such as magnesium or calcium stearate, and/or polyethylene glycol. Dragée cores are provided with suitable coatings that are optionally resistant to gastric juice, there being used, inter alia, concentrated sugar solutions, which optionally contain gum arabic, talc, polyvinylpyrrolidone, polyethylene glycol and/or titanium dioxide, or lacquer solutions in suitable organic solvents or solvent mixtures or, for the manufacture of gastric juice-resistant coatings, solutions of suitable cellulose preparations, such as acetylcellulose phthalate or hydroxypropylmethylcellulose phthalate. Colouring substances or pigments can be added to the tablets or dragée coatings, for example for the purpose of identification or for characterising different doses of active ingredient.

Other, orally administrable, pharmaceutical dose units are push-fit capsules made of gelatin as well as soft sealed capsules made of gelatin and a plasticiser, such as glycerin or sorbitol. The push-fit capsules can contain the active ingredient in the form of a granulate, for example in a mixture with fillers, such as lactose, binders, such as starches, and/or lubricants, such as talc or magnesium stearate, and optionally stabilisers. In soft capsules the active ingredient is preferably dissolved or suspended in suitable liquids, such as fatty oils, paraffin oil or liquid polyethylene glycols, it likewise being possible for stabilisers to be added.

There come into consideration as rectally administrable pharmaceutical compositions, for example suppositories that consist of a combination of the active ingredient with a suppository base substance. Suitable suppository base substances are, for example, natural or synthetic triglycerides, parrafin hydrocarbns, polyethylene glycols or higher alkanols. It is also possible to use gelatin rectal capsules that contain a combination of the active ingredient with a base substance; there come into consideration as base substances, for example, liquid triglycerides, polyethylene glycols or paraffin hydrocarbons.

There are suitable for parenteral administration especially aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides; or aqueous injection suspensions that contain substances that increase viscosity, for example sodium carboxymethylcellulose, sorbitol and/or dextran, and optionally stabilisers.

The invention relates also to the use of the novel compounds of the formula I and pharmaceutically acceptable salts of such compounds as pharmacologically active compounds, especially as diuretics having uricosuric action in addition, preferably in the from of pharmaceutical compositions, in a method for the prophylactic and/or therapeutic treatment of the animal or human body, especially for the treatment of oedema or hypertension.

The following Examples illustrate the above-described invention but are not intended to limit the scope thereof in any way. Temperatures are in degrees Centigrade.

EXAMPLE 1

25.43 g (0.10 mole) of 2,3-dihydro-5,6-dihydroxy-2-methyl-2-phenyl-1H-inden-1-one and 15.7 g (12.3 ml, 0.10 mole) of dichloroacetic acid ethyl ester are boiled under reflux with 70 g (0.5 mole) of pulverised anhydrous potassium carbonate in 250 ml of 1,2-dimethoxyethane for 2 hours in a nitrogen atmosphere while stirring vigorously, during the course of which the initial suspension turns into a dark solution from which a dark grease is deposited around the edge of the vessel. After cooling, 250 ml of water are added and the dark solution is stirred at 40° C. for one hour. The 1,2-dimethoxyethane is then evaporated off in vacuo and the remaining aqueous solution is rendered acidic to Congo Red by the gradual addition of 6N hydrochloric acid. The resuting carboxylic acid is extracted with ethyl acetate. The ethyl acetate solution is in turn extracted with 1N sodium bicarbonate solution, the latter solution is again rendered acidic to Congo Red with 6N hydrochloric acid, the carboxylic acid is again taken up in ethyl acetate and the resulting solution is concentrated by evaporation. The carboxylic acid which remains is dissolved in 55 ml of 2N sodium hydroxide solution, fuller's earth is added to the solution and filtration is carried out. By cooling the filtrate in an ice bath and inoculating, the sodium salt of 6,7-dihydro-6-methyl-5-oxo-6-phenyl-5H-indeno[5,6-d]-1,3-dioxole-2-carboxylic acid is caused to crystallise into platelets that are difficult to filter. These are removed by filtering through a cellulose filter, washed with a little ice-cold water and dried for 20 hours at room temperature under 100 mbar. The resulting sodium salt melts at a temperature of about 50° C. with decomposition.

Formula of the acid:

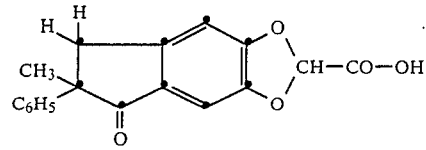

The required indenone derivative is produced as follows:

(a) In the course of 10 minutes 50 ml (0.52 mole) of acetic anhydride are added dropwise at room temperature, while stirring, to a mixture of 25.6 g (0.1 mole) of 1-(3,4-dimethoxyphenyl)-2-phenyl-1-ethanone [cf. S. F. Dyke et al., Tetrahedron 31, 1219–1222 (1975)] and 50 ml (approximately 0.4 mole) of bis-(dimethylamino)-methane, care being taken that the temperature of the reaction mixture does not exceed 40° C. by cooling by means of an ice bath. The resulting yellowish solution is then stirred for a further hour, the internal temperature being allowed to drop to room temperature. Subsequently, the reaction solution, with vigorous stirring and inoculation, is cautiously poured into a mixture of ice and water, with the result that a readily filterable suspension forms. The crystallised 1-(3,4-dimethoxyphenyl)-2-phenyl-2-propen-1-one is filtered off at 10° and dried for 18 hours at 40° under 130 mbar; m.p. 74°–75.5°. Owing to its low stability, the substance is further processed as quickly as possible.

(b) 13.4 g of 1-(3,4-dimethoxyphenyl)-2-phenyl-2-propen-1-one are added in portions in the course of 5 minutes at 95°, while stirring, to 135 ml (approximately 275 g) of polyphosporic acid. With slight self-heating to approximately 100°, a pale brown solution forms. When the addition is complete, the solution is stirred for a further half hour at 95°–100° and then cooled to room temperature. While stirring and cooling with ice, 300 ml of water are cautiously added dropwise in such a manner that the internal temperature remains below 40°. The resulting greenish suspension is filtered by suction, the suction-filtered material is washed with water and then dried at 40° for one hour. The 2,3-dihydro-5,6-dimethoxy-2-phenyl-1H-inden-1-one so obtained melts at 149°–152° and, after recrystallisation from acetone/ethyl acetate, at 154°–155°.

(c) A solution of 126.7 g (0.47 mole) of 2,3-dihydro-5,6-dimethoxy-2-phenyl-1H-inden-1-one and 142 g (62.5 ml, 0.994 mole) of methyl iodide in 2000 ml of methylene chloride is added dropwise in the course of one hour at room temperature, while stirring, to 330 ml of a 40% aqueous solution of tetrabutylammonium hydroxide (approximately 0.5 mole). With gentle heating a yellowish suspension forms. This is stirred at room temperature for a further 6 hours. The phases are then separated, the organic phase is washed twice with water, dried, filtered and concentrated by evaporation. The residue is dissolved in 300 ml of ethanol while heating. During the course of this and on subsequent cooling 2,3-dihydro-5,6-dimethoxy-2-methyl-2-phenyl-1H-inden-1-one crystallises. It is filtered, washed with a cold mixture of ethanol and petroleum ether (boiling range 40°–65°) and dried at 40° under approximately 130 mbar for 18 hours. M.p. 132°–133°.

By concentrating the mother liquor by evaporation and adding approximately 200 ml of ether, the tetrabutylammonium iodide can be obtained in the form of crystals.

(d) 5.6 g (0.020 mole) of 2,3-dihydro-5,6-dimethoxy-2-methyl-2-phenyl-1H-inden-1-one are heated for 5 hours at 110° in a mixture of 22.7 ml (0.2 mole) of 48% strength hydrobromic acid and 25 ml of anhydrous acetic acid, then 2 ml of a 33% strength hydrogen bromide solution in acetic acid are added and the mixture is heated again at 110° for 8 hours. After cooling, the reaction mixture is poured into ice-water and extracted twice with ether. The combined ethereal solutions are washed twice with water, once with aqueous 1N sodium bicarbonate solution and a further twice with water, dried, filtered and concentrated by evaporation. The crude 2,3-dihydro-5,6-dihydroxy-2-methyl-2-phenyl-1H-inden-1-one which remains can be further processed directly.

EXAMPLE 2

26.83 g (0.10 mole) of 2,3-dihydro-4,5-dihydroxy-2,7-dimethyl-2-phenyl-1H-inden-1-one and 15.7 g (12.3 ml, 0.10 mole) of dichloroacetic acid ethyl ester are boiled under reflux for 4 hours in a nitrogen atmosphere, while stirring vigorously, with 70 g (0.5 mole) of pulverised anhydrous potassium carbonate in 300 ml of 1,2-dimethoxyethane. The reaction mixture is then cooled to 40°, 300 ml of water are added and the mixture is stirred for one hour at 35°-40°. The 1,2-dimethoxyethane is then evaporated off in vacuo in a rotary evaporator and the remaining solution is rendered acidic to Congo Red in the cold by the cautious addition of 6N hydrochloric acid. The resulting acid is extracted with ethyl acetate, the ethyl acetate solution is washed twice with water, dried, filtered and concentrated by evaporation. A sample of the residue, which has solidified in the form of a foam, is recrystallised from toluene; the 7,8-dihydro-5,7-dimethyl-6-oxo-7-phenyl-6H-indeno[4,5-d]-1,3-dioxole-2-carboxylic acid so obtained melts at 161°-163° (after sintering from 159°). The residue which remains is dissolved in 40 ml of 2N sodium hydroxide solution while heating, fuller's earth is added to the warm solution, and this is filtered in the warm and then cooled in an ice bath. The sodium salt of 7,8-dihydro-5,7-dimethyl-6-oxo-7-phenyl-6H-indeno-[4,5-d]-1,3-dioxole-2-carboxylic acid which crystallises out in the form of small fine needles is filtered, washed with ice-cold water and dried for 15 hours at 30° under 0.13 mbar. It melts at 187°-190°.

Formula:

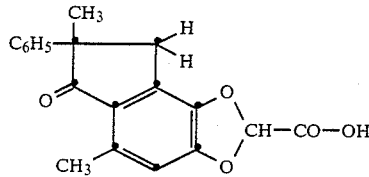

By acidification of the mother liquor, extraction with ether and concentration by evaporation in vacuo, the corresponding diastereoisomeric acid is obtained in the form of an amorphous foam.

The required indenone derivative is produced as follows:

(a) 80.0 g (0.6 mole) of aluminium chloride are introduced in portions, while stirring, into a solution of 84.1 g (0.5 mole) of 1,2-dimethoxy-4-methylbenzene (homopyrocatechol dimethyl ether or 4-methylveratrole) in 750 ml of 1,2-dichloroethane, during which the temperature is maintained at 20° maximum by cooling with an ice bath. Then, at 15°-20°, 85.0 g (approximately 73 ml, 0.55 mole) of phenyl acetyl chloride are added dropwise in the course of one hour, during which there is moderate evolution of hydrogen chloride and the aluminium chloride is dissolved.

The reaction mixture is then stirred at room temperature for a further 6 hours and subsequently poured into 3000 ml of a mixture of ice and water. The resulting layers are separated and the organic phase is washed in succession with 2N hydrochloric acid, twice with water, then with 1N sodium bicarbonate solution and a further twice with water, dried, filtered and concentrated by evaporation. The partially crystallised residue is caused to crystallise completely from ether/petroleum ether (boiling range 40°-65°), 1-(4,5-dimethoxy-2-methylphenyl)-2-phenyl-1-ethanone having a melting point of 45°-48° being obtained.

(b) 240 ml of acetic anhydride are added dropwise in the course of 20 minutes at room temperature, while stirring, to a mixture of 135.0 g (0.50 mole) of 1-(4,5-dimethoxy-2-methylphenyl)-2-phenyl-1-ethanone and 250 ml of bis-(di-methylamino)-methane, the temperature being held at 40° by cooling with an ice bath. The reaction mixture is stirred at 40° for a further hour and is then poured into a 2 kg mixture of ice and water, during which the crude product crystallises. After stirring for 15 minutes at 15° the crude product is filtered off, the filtered material is washed with cold water and then dried for 18 hours at 30° under approximately 100 mbar, yielding 1-(4,5-dimethoxy-2-methylphenyl)-2-phenyl-2-propen-1-one having a melting point of 57°-59°.

(c) 70.0 g (0.25 mole) of the crystallised product of (b) are sprinkled in the course of 2 to 3 minutes, while stirring and without supplying heat, into 700 ml of polyphosphoric acid which has been heated to 90°. In the course of this the temperature rises to approximately 95° and a violet mixture forms. This is then immediately heated to 105° and is stirred for a further 15 minutes at 105°-110°. It is then cooled to 40° and, while stirring, 1000 ml of toluene and 300 ml of methylene chloride, and then 3 kg of ice, are added and the mixture is further stirred at 10°-20° until a homogeneous emulsion is formed. The layers are then separated and the organic phase is washed once with saturated sodium bicarbonate solution and twice with water. The solution of 2,3-dihydro-4,5-dimethoxy-7-methyl-2-phenyl-1H-inden-1-one obtained as organic phase can be used directly for the next stage.

(d) The solution obtained according to (c) of approximately 0.25 mole of the indenone derivative obtained according to (c), to which 42.6 g (18.7 ml, 0.3 mole) of methyl iodide are first added, is added in the course of 25 minutes at room temperature, while stirring and cooling by means of a water bath, to a mixture of 96.5 g of tetrabutylammonium bromide and 60 ml of concentrated (approximately 10N) sodium hydroxide solution, and the mixture is stirred, its temperature initially rising slightly, for a further 4 hours without supplying heat. The organic phase is then separated off, washed three times with water, dried over sodium sulphate, filtered and concentrated by evaporation to approximately 300 ml. At 20°, the precipitated mixture of tetrabutylammonium bromide and iodide is filtered off and washed with toluene. The filtrate is concentrated to dryness by evaporation and an approximately tenfold amount of ether is added to the residue. After leaving to stand in an ice bath for one hour, the yellowish crystals are filtered off. The 2,3-dihydro-4,5-dimethoxy-2,7-dimethyl-2-phenyl-1H-inden-1-one so obtained melts at 94°–95°.

(e) A mixture of 29.6 g (0.10 mole) of the indenone derivative obtained according to (d), 115 ml of 48% strength hydrobromic acid, 100 ml of anhydrous acetic acid and 25 ml of a 33% strength solution of hydrogen bromide in acetic acid is boiled under reflux for 8 hours in a nitrogen atmosphere and, after cooling, poured into a 1500 g mixture of ice and water and extracted twice with ether. The combined ethereal phases are washed with water, then with 1N sodium bicarbonate solution and a further twice with water, dried over sodium sulphate, filtered and concentrated by evaporation. The brownish residue crystallises after standing for a relatively long time. It is dissolved in ether while heating, fuller's earth is added and filtration is carried out. Cyclohexane is added to the filtrate, the ether is partially evaporated off in a rotary evaporator and the solution is inoculated with the desired substance, crystallisation occurring. After the addition of a little petroleum ether, the ether is evaporated off further and then the 2,3-dihydro-4,5-dihydroxy-2,7-dimethyl-2-phenyl-1H-inden-1-one which has crystallised out is filtered off. It melts at 160°–163°.

EXAMPLE 3

Analogously to Example 2, using 27.21 g (0.10 mole) of 2,3-dihydro-5,6-dihydroxy-2-(4-fluorophenyl)-2-methyl-1H-inden-1-one and 15.7 g (0.10 mole) of dichloroacetic acid ethyl ester as starting materials, the sodium salt of 6,7-dihydro-6-(4-fluorophenyl)-6-methyl-5-oxo-5H-indeno[5,6-d]-1,3-dioxole-2-carboxylic acid, which after leaving to stand for a relatively long time in the cold in the form of its aqueous solution crystallises into fine platelets, is obtained, which after recrystallisation from water/acetone with removal by distillation of the acetone is obtained in the form of the trihydrate which melts at a temperature of about 50°.

The indenone derivative used as starting material is produced as follows:

(a) 160 g (1.2 mole) of pulverised aluminium chloride are suspended in 1500 ml of 1,2-dichloroethane and the suspension is cooled to 10°. Then, while stirring, 139.0 g (1.0 mole) of veratrole are added all at once, the temperature rising to 28° and a large proportion of the aluminium chloride dissolving. Subsequently, at 20° and while stirring, 190.9 g (1.1 mole) of (4-fluorophenyl)-acetyl chloride are added dropwise in the course of one hour. With moderate evolution of hydrogen chloride and slight exothermic reaction, the reaction solution becomes dark-coloured. It is then stirred for a further 1½ hours at room temperature and is subsequently poured into a 2 kg mixture of ice and water and 50 ml of concentrated hydrochloric acid are added. The organic phase is separated off and washed once with 2N hydrochloric acid, twice with water, once with 1N sodium bicarbonate solution and twice with water. The aqueous phase is extracted once with chloroform and the residue obtained after evaporating off the chloroform is added to the organic phase. The resulting mixture is filtered and concentrated by evaporation in vacuo, approximately 300 ml of cyclohexane are added to the still warm oily residue, and the mixture is shaken vigorously so that a readily filterable crystalline suspension results. After cooling, this is filtered and the filtered material is washed with cyclohexane. The 1-(3,4-dimethoxyphenyl)-2-(4-fluorophenyl)-1-ethanone so obtained melts at 102°–104° after sintering from 100°.

(b) Analogously to Example 2(b), using 109.7 g (0.40 mole) of 1-(3,4-dimethoxyphenyl)-2-(4-fluorophenyl)-1-ethanone, 1-(3,4-dimethoxyphenyl)-2-(4-fluorophenyl)-2-propen-1-one is obtained, which precipitates in the form of colourless crystals when the reaction mixture is poured into a mixture of ice and water and, after drying for 16 hours at 40° under approximately 130 mbar, melts at 77°–78°.

(c) Analogously to Example 2(c), using 85.9 g (0.30 mole) of 1-(3,4-dimethoxyphenyl)-2-(4-fluorophenyl)-2-propen-1-one, 2,3-dihydro-5,6-dimethoxy-2-(4-fluorophenyl)-1H-inden-1-one is obtained, which crystallises on adding water to the reaction mixture. The crystals are washed with water and dried and then dissolved in 2500 ml of methylene chloride. The solution is decanted to remove deposited black-green resin, fuller's earth is added, filtration is carried out, the filtrate is concentrated to approximately 500 ml and approximately 500 ml of ethyl acetate are added to the resulting suspension. After distilling off the remaining methylene chloride, the suspension is cooled and the crystals of the above reaction product are filtered off and washed with ethyl acetate; m.p. 189°–191°.

(d) Analogously to Example 2(d), using 47.7 g (0.167 mole) of 2,3-dihydro-5,6-dimethoxy-2-(4-fluorophenyl)-1H-inden-1-one, crude 2,3-dihydro-5,6-dimethoxy-2-(4-fluorophenyl)-2-methyl-1H-inden-1-one is obtained. There is added to the residue obtained by concentration by evaporation of the organic phase 120 ml of ethanol instead of ether and, after scratching, the reaction product crystallises out in the form of small fine needles. After cooling, the needles are filtered and washed with ethanol/ether and dried for 16 hours at 40° under 130 mbar, whereupon they then have a melting point of 100°–101°.

(e) Analogously to Example 2(e), using 30.0 g (0.10 mole) of the product of (d), crude 2,3-dihydro-5,6-dihydroxy-2-(4-fluorophenyl)-2-methyl-1H-inden-1-one is obtained in the form of a solidified foam. The product can be further processed directly.

EXAMPLE 4

Analogously to Example 2, using 28.64 g (0.10 mole) of 2,3-dihydro-4,5-dihydroxy-2,7-dimethyl-2-(4-fluorophenyl)-1H-inden-1-one, the sodium salt of 7,8-dihydro-5,7-dimethyl-7-(4-fluorophenyl)-6-oxo-6H-indeno[4,5-d]-1,3-dioxole-2-carboxylic acid is obtained in the form of the monohydrate having a melting point of 188°–190°.

The required indenone derivative is produced as follows:

(a) A solution of 1682 g (1.0 mole) of 1,2-dimethoxy-4-methylbenzene in 1500 ml of 1,2-dichloroethane is precooled in an ice bath and, while stirring, 160 g (1.2 mole) of pulverised aluminium chloride are added in portions. Then, while stirring at 15°–20°, 190 g (1.1 mole) of (4-fluorophenyl)-acetyl chloride are added dropwise in the course of 30 minutes, during which moderate evolution of hydrogen chloride occurs and the aluminium chloride is dissolved. After stirring for a further 5 hours at room temperature, the reaction mixture is poured into an approximately 5 kg mixture of ice and water. The phases are separated in a separating funnel and the aqueous phase is extracted twice with methylene chloride and the residue of the methylene chloride solution obtained by concentration by evaporation is added to the organic phase. The resulting mixture is washed in succession with 2N hydrochloric acid, twice with water, twice with saturated sodium bicarbonate solution with subsequent filtration through fuller's earth, and twice more with water, dried over sodium sulphate, filtered and concentrated by evaporation. The still warm residue is dissolved in ether and the ethereal solution is concentrated to approximately 700 ml by evaporation. On cooling, 2-(4-fluorophenyl)-1-(4,5-dimethoxy-2-methylphenyl)-1-ethanone crystallises. It is filtered by suction and then washed with cold ether; m.p. 96°–97°.

(b) Analogously to Example 1(b), using 115.3 g (0.40 mole) of 2-(4-fluorophenyl)-1-(4,5-dimethoxy-2-methylphenyl)-1-ethanone, crude 2-(4-fluorophenyl)-1-(4,5-dimethoxy-2-methylphenyl)-2-propen-1-one is obtained, which is directly further processed.

(c) Analogously to Example 2(c), using the crude product of (b) (115 g, approximately 0.4 mole), crude 2,3-dihydro-4,5-dimethoxy-2-(4-fluorophenyl)-7-methyl-1H-inden-1-one is obtained.

(d) Analogously to Example 2(d), using 50.1 g (0.167 mole) of the indenone derivative obtained according to (c), 2,3-dihydro-4,5-dimethoxy-2,7-dimethyl-2-(4-fluorophenyl)-1H-inden-1-one is obtained in the form of a pale sand-coloured powder having a melting point of 102°–104°.

(e) Analogously to Example 2(e), using 31.44 g (0.10 mole) of the reaction product of (d), 2,3-dihydro-4,5-dihydroxy-2,7-dimethyl-2-(4-fluorophenyl)-1H-inden-1-one is obtained in the form of a pale brown powder having a melting point of 189°–190°.

EXAMPLE 5

By reacting 43.0 g (0.15 mole) of 2,3-dihydro-4,5-dihydroxy-2,7-dimethyl-2-(2-fluorophenyl)-1H-inden-1-one [prepared analogously to Examples 4(a), 1(b), 2(c), 2(d) and 2(e)] with 23.8 g (0.15 mole) of dichloroacetic acid ethyl ester in the presence of 105 g (0.75 mole) of pulverised anhydrous potassium carbonate in 430 ml of 1,2-dimethoxyethane, there is obtained analogously to Example 2 crude 7,8-dihydro-5,7-dimethyl-7-(2-fluorophenyl)-6-oxo-6H-indeno[4,5-d]-1,3-dioxole-2-carboxylic acid in the form of the residue of the ethyl acetate solution obtained by concentration by evaporation. The crude acid can be purified, for example, as follows: the residue obtained by concentration by evaporation is dissolved in 500 ml of 1N sodium hydroxide solution, aqueous calcium chloride solution is added until the rate of precipitation is only slow and the precipitate is filtered through fuller's earth. The filtrate is acidified with 2N hydrochloric acid and extracted with ethyl acetate. The ethyl acetate solution is again concentrated by evaporation, the residue is dissolved in 2N sodium hydroxide solution, the solution is acidified with 2N hydrochloric acid and stirred vigorously for 2 hours, the precipitate is filtered off, washed with water and dried for 40 hours at 40° under 130 mbar. The resulting brittle amorphous substance melts at a temperature of above 90° and gives analysis results appropriate for the desired carboxylic acid.

EXAMPLE 6

6.50 g (0.062 mole) of 7,8-dihydro-5,7-dimethyl-6-oxo-7-phenyl-6H-indeno[4,5-d]-1,3-dioxole-2-carboxylic acid (freed in customary manner from the sodium salt described in Example 2) are dissolved in 130 ml of anhydrous ethanol, 0.1 ml of a 5N hydrogen chloride solution in ether is added to the solution and the mixture is boiled under reflux for one hour. The reaction mixture is then concentrated by evaporation, the residue is taken up in ether and the ethereal solution is washed once with 1N sodium bicarbonate solution and once with water, dried over sodium sulphate, filtered and concentrated by evaporation. The residue, which has already crystallised, is recrystallised from ethanol, resulting in 7,8-dihydro-5,7-dimethyl-6-oxo-7-phenyl-6H-indeno[4,5-d]-1,3-dioxole-2-carboxylic acid ethyl ester in the form of small colourless needles having a melting point of 96°–97°. This diastereoisomeric ester exhibits the following signals in the NMR spectrum: 1.34 ppm (3H t), 1.63 ppm (3H s), 2.59 ppm (3H s), 3.14 ppm (1H d), 3.52 ppm (1H d), 4.34 ppm (2H q), 6.38 ppm (1H s), 6.76 ppm (1H s), approximately 7.27 ppm (5H m).

The diastereoisomeric acid freed from the mother liquor of the sodium salt of the above acid of Example 2 and isolated in that Example in the form of a foam, can be converted analogously to the above process into the diastereoisomeric ethyl ester which, unlike the free acid, can by crystallised and recrystallised from ethanol and then melts at 93°–94°. In the NMR spectrum this diastereoisomeric ester exhibits the following signals: 1.37 ppm (3H t), 1.65 ppm (3H s), 2.61 ppm (3H s), 3.20 ppm (1H d), 3.48 ppm (1H d), 4.34 ppm (2H q), 6.39 ppm (1H s), 6.75 ppm (1H s), approximately 7.27 ppm (5H m).

EXAMPLE 7

(a) A solution of 19.9 g (61.36 mmoles) of the racemic 7,8-dihydro-5,7-dimethyl-6-oxo-7-phenyl-6H-indeno[4,5-d]-1,3-dioxole-2-carboxylic acid having a melting point of 161°–163° obtained according to Example 2, 8.76 g (30.7 mmoles) of (+)-dehydroabietylamine and 3.1 g (30.6 mmoles) of triethylamine in a mixture of 85 ml of methanol and 8.5 ml of water is left to stand for several hours at room temperature and then while cooling with ice and, subsequently, the resulting dehydroabietylamine salt is filtered off and, after recrystallisation twice from 20 times the amount of a mixture of 9 parts methanol and one part water, exhibits the following melting properties:

(A) On heating slowly at <5°/min, a melting point of 138°–139° results;

(B) On introducing into the melting point-determining apparatus, which has been preheated to 120°, and rapidly heating further at approximately 5°/min, a melting point of 178°–180° results, before which a nematic phase occurs.

If the dextrorotatory acid is freed from the above dehydroabietylamine salt in known manner, then it is obtained in the form of an amorphous foam which exhibits the following rotatory values:

$[\alpha]_D^{20} + 47°$ (c=1%, acetone)
$[\alpha]_{436}^{20} + 193°$ (b) From the salts (predominantly triethylamine salt) remaining in the mother liquor from the above separation, again the acid is freed and isolated in customary manner and subsequently, in acetonitrile as solvent, one equivalent of (−)-ephedrine is added. The (−)-ephedrine salt, which is filtered off after leaving to stand for several hours and then cooling with ice, exhibits a melting point of 166°–167° after recrystallisation three times from acetonitrile. If the acid is freed from this salt it is obtained in the form of an amorphous foam with the following rotatory values:

$[\alpha]_D^{20} -45°$ (c=1%, acetone)
$[\alpha]_{436}^{20} -190°$ (c) The separation can also be carried out by first of all treating the racemic acid appropriately with (−)-ephedrine and triethylamine in acetonitrile, separating off the (−)-ephedrine salt of the levorotatory acid and, from the remaining mother liquors, converting the concentrated dextrorotatory acid with (+)-dehydroabietylamine into the corresponding salt and purifying the latter by recrystallisation.

EXAMPLE 8

(a) A solution of (+)-2,3-dihydro-4,5-dihydroxy-2,7-dimethyl-2-phenyl-1H-inden-1-one in 35.5 ml of 2N potassium hydroxide solution is added dropwise in the course of one hour to a mixture, stirred at 80° under a nitrogen atmosphere, of 17.3 g of dichloroacetic acid in 72 ml of aqueous 5N potassium hydroxide solution and 0.3 g of tri-($C_8$-$C_{10}$-alkyl)-methylammonium chloride. The reaction mixture is subsequently stirred for 8 hours at 80°, then cooled, acidified with 6N hydrochloric acid and the acids are extracted with ether. The ethereal extract is concentrated by evaporation and the residue is dissolved in 150 ml of absolute ethanol. 0.5 ml of ethereal 5N hydrogen chloride solution is added and the solution is boiled under reflux for one hour, then concentrated to dryness by evaporation in vacuo, and the residue is taken up in ether again. The ethereal solution is washed once with dilute aqueous solution bicarbonate solution and once with water, then dried over sodium sulphate, filtered and concentrated by evaporation. The crude residue obtained by concentration by evaporation is filtered with the aid of a solvent mixture of chloroform (10 parts), hexane (10 parts) and ethyl acetate (1 part) over a bed of 140 g of silica gel, and the filtrate purified in this manner is again concentrated to dryness by evaporation. 20 ml of aqueous 2N sodium hydroxide solution are added to the residue of 13.0 g obtained by concentration by evaporation and the mixture is heated on a water bath until dissolution occurs. After leaving to stand for one hour at room temperature, the solution is rendered acidic with 2N hydrochloric acid and the resulting acids are extracted with ether. Concentration of the ethereal extracts by evaporation in vacuo yields the crude acids in the form of an almost colourless brittle amorphous foam, consisting of the two diastereoisomeric dextrorotatory antipodes of 7,8-dihydro-5,7-dimethyl-6-oxo-7-phenyl-6H-indeno]4,5-d]-1,3-dioxole-2-carboxylic acid.

(b) A solution of 4.88 g (17.1 mmole) of (+)-dehydroabietylamine and 1.73 g (17.1 mmoles) of triethylamine in 50 ml of methanol is added to 11.1 g (34.2 mmoles) of the acid mixture obtained according to (a). After leaving to stand for a few hours in an ice bath, the dehydroabietylamine salt of one of the diastereoisomers crystallises out in the form of small fine needles and can be removed by filtration. (The salt is identical in all of its properties to the (+)-dehydroabietylamine salt obtained according to Example 7(a)). The filtrate is concentrated to dryness by evaporation and the acid is freed from the residue. 6.9 g of amorphous foam are obtained, approximately 90% consisting of the strongly dextrorotatory diastereoisomer of 7,8-dihydro-5,7-dimethyl-6-oxo-7-phenyl-6H-indeno-[4,5-d]-1,3-dioxole-2-carboxylic acid having the following rotatory values:

$[\alpha]_D^{20} +166°$ (c32 1%, acetone)
$[\alpha]_{436}^{20} +478°$ (c) For further removal of diastereoisomeric impurities, the acid obtained according to (b) is converted with (−)-menthol into the menthol ester according to a known esterification method, for example: Chem. Ber. 95, page 1284 ff (1962), H. A. Staab and A. Mannschreck, and the menthol ester is purified by medium pressure liquid chromatography. The ester of the strongly dextrorotatory form with (−)-menthol exhibits a melting point of 108°–109° (recrystallised from hexane).

(d) 0.5 g of the pure menthol ester obtained according to (c) is stirred in a mixture of 2 ml of 1N sodium hydroxide solution, 5 ml of water and 20 ml of methanol for 2 hours a 60°. For working up, the methanol is evaporated off in vacuo and the residue is diluted with water. The aqueous phase is extracted twice with ether. The aqueous phase is then rendered acidic with dilute hydrochloric acid and the resulting acid is extracted with ether. The ethereal solution is dried over sodium sulphate, filtered and concentrated to dryness by evaporation in vacuo in a rotary evaporator. The strongly dextrorotatory form of the 7,8-dihydro-5,7-dimethyl-6-oxo-7-phenyl-6H-indeno-[4,5-d]-1,3-dioxole-2-carboxylic acid remains, in the form of a colourless amorphous foam, and exhibits in this pure state the following rotatory values:

$[\alpha]_D^{20} +213°$ (c=1%, acetone)
$[\alpha]_{436}^{20} +604°$ (e) By suitable analogous procedures it is possible to obtain from the levorotatory phenoxyacetic acid obtained according to (i), analogously to the steps (k) and (a) to (d), the strongly levorotatory form of 7,8-dihydro-5,7-dimethyl-6-oxo-7-phenyl-6H-indeno[4,5-d]-1,3-dioxole-2-carboxylic acid.

The optically active starting material for stage (a) can be obtained as follows:

(f) 141.7 g (0.478 mole) of the 2,3-dihydro-4,5-dimethoxy-2,7-dimethyl-2-phenyl-1H-inden-1-one obtained according to Example 2(d) are boiled under slight reflux for 45 minutes with a mixture of 275 ml of aqueous 48% strength hydrobromic acid, 475 ml of glacial acetic acid and 72 ml of 33% strength hydrogen bromide in glacial acetic acid and then the reaction mixture is poured into 3000 ml of a mixture of ice and water. The product so obtained is extracted twice with ether and the ethereal phases are washed once with water, once with dilute sodium bicarbonate solution, and twice with water again. The ethereal phases are dried over sodium sulphate, filtered, and concentrated to dryness by evaporation in vacuo in a rotary evaporator. The crude residue of 135 g of brown crystals is dissolved warm in 250 ml of ethyl acetate and filtered. Subsequently, 500 ml of petroleum ether having a boiling range of 40°–60° are added. On leaving to stand, the product crystallises out and can be filtered and dried. In this manner 2,3-dihydro-2,7-dimethyl-4-hydroxy-5-methoxy-2-phenyl-1H-inden-1-one having a melting point of 136°–139° is obtained.

(g) 42.3 g (0.15 mole) of the 4-hydroxy compound obtained according to (e) are vigorously stirred for ½ hour at 60° together with 28 g of anhydrous pulverised potassium carbonate and 32.3 g (0.19 mole) of bromoacetic acid ethyl ester in 400 ml of dimethylformamide. Subsequently, 400 ml of water and 80 ml of concentrated aqueous sodium hydroxide solution are added to the resulting suspension and the solution formed is heated for one hour at 90°. 400 g of ice are added to the now pale yellow solution, the solution is rendered acidic with concentrated hydrochloric acid and the precipitated product is extracted with ether. The ethereal extract is dried over sodium sulphate, filtered and concentrated, and the reaction product begins to precipitate in crystalline form. To complete the crystallisation, cooling in an ice bath is carried out and the crystals are then filtered off, 2-(2,3-dihydro-2,7-dimethyl-5-methoxy-2-phenyl-1H-inden-4-yloxy)-acetic acid having a melting point of 151°–152° being obtained.

(h) 92.6 g (0.272 mole) of the racemic acid obtained according to (g) are dissolved together with 13.8 g (0.136 mole) of triethylamine and 16.5 g (0.136 mole) of S-(−)-1-phenylethylamine in 300 ml of acetonitrile. The salt with S-(−)-1-phenylethylamime, which crystallises at room temperature, is filtered off and repeatedly recrystallised from acetonitrile until its melting point, initially 142°–144°, has risen to 160°–161°. If the dextrorotatory 2-(2,3-dihydro-2,7-dimethyl-5-methoxy-2-phenyl-1H-inden-4-yloxy)-acetic acid is now freed from this salt in known manner, an amorphous foam with the following rotatory values is obtained:

$[\alpha]_D^{20} + 103°$ (c=1%, in acetone)
$[\alpha]_{436}^{20} + 316°$ (i) By analogous procedure, using R(+)-1-phenylethylamine, the levorotatory 2-(2,3-dihydro-2,7-dimethyl-5-methoxy-2-phenyl-1H-inden-4-yloxy)-acetic acid with the following rotatory values is obtained:

$[\alpha]_D^{20} - 106°$ (c=1%, in acetone)
$[\alpha]_{436}^{20} - 326°$ (k) 15.2 g (44.7 moles) of the dextrorotatory phenoxyacetic acid obtained according to (h) are mixed with 80 g of pyridine-hydrochloride and immersed in a bath pre-heated to 200°. The resulting melt is stirred at the same temperature for 4½ hours, then the still hot melt is poured onto 500 g of ice to which 50 ml of 6N hydrochloric acid have previously been added. The resulting product is extracted with ether. The ethereal extracts are washed twice with water, dried over sodium sulphate, filtered and concentrated to dryness by evaporation. A dextrorotatory 2,3-dihydro-4,5-dihydroxy-2,7-dimethyl-2-phenyl-1H-inden-1-one in the form of a sand-coloured foam with the following rotatory values is obtained:

$[\alpha]_D^{20} + 98°$ (c=1%, acetone)
$[\alpha]_{436}^{20} + 304°$.

EXAMPLE 9

Tablets containing 100 mg of active ingredient can be produced, for example, with the following composition:

| Composition | per tablet |
|---|---|
| sodium salt of 7,8-dihydro-5,7-dimethyl-6-oxo-7-phenyl-6H-indeno-[4,5-d]-1,3-dioxole-2-carboxylic acid | 100 mg |
| lactose | 50 mg |
| wheat starch | 73 mg |
| colloidal silica | 13 mg |
| talc | 12 mg |
| magnesium stearate | 2 mg |
| | 250 mg |

Manufacture

The active ingredient is mixed with the lactose, a portion of the wheat starch and with the colloidal silica and the mixture is forced through a sieve. A further portion of the wheat starch is made into a paste with 5 times the amount of water on a water bath and the powder mixture is kneaded with this paste until a slightly plastic mass is obtained. The mass is forced through a sieve having a mesh width of approximately 3 mm, dried, and the dried granulate is forced through a sieve again. Then, the remaining wheat starch, the talc and the magnesium stearate are admixed. The resulting mixture is pressed into tablets each weighing 250 mg and having (a) break notch(es).

EXAMPLE 10

To produce 1000 capsules each containing 100 mg of active ingredient, 100 g of 7,8-dihydro-5,7-dimethyl-6-oxo-7-phenyl-6H-indeno[4,5-d]-1,3-dioxole-2-carboxylic acid is mixed with 173.0 g of lactose, the mixture is uniformly moistened with an aqueous solution of 2.0 g of gelatin and granulated through a suitable sieve (for example sieve III according to Ph.Helv.V.). The granulate is mixed with 10.0 g of dried corn starch and 15.0 g of talc and 1000 size 1 hard gelatin capsules are filled with equal quantities of this mixture.

Instead of the active ingredient used above, it is also possible to use in Examples 9 and 10 another compound of the general formula I, or a salt of a compound of the general formula I capable of salt formation, for example one of the substances described in Examples 1 and 3 to 8.

What is claimed is:

1. A dioxaheterocyclic compound of the formula I

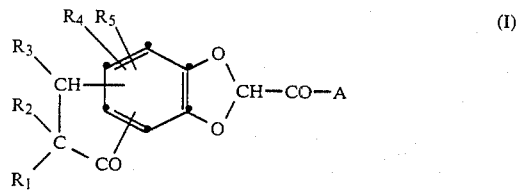

in which $R_1$ represents phenyl or pyridyl each of which is unsubstituted or substituted by lower alkyl, lower alkoxy or halogen, $R_2$ represents primary lower alkyl, each of $R_3$ and $R_4$ represents, independently of the other, hydrogen or lower alkyl, $R_5$ represents hydrogen and A represents the radical —O—$R_6$ in which $R_6$ represents hydrogen or an unsubstituted or substituted aliphatic or araliphatic hydrocarbon radical or the radical

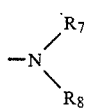

in which each of $R_7$ and $R_8$, independently of the other, represents hydrogen or lower alkyl, or, $R_7$ and $R_8$ are bonded to one another and, together with the adjacent nitrogen atom, represent unsubstituted or lower alkyl-substituted tetra- to hexa-methylene-imino or 4-morpholinyl, and the divalent radical in formula I is either in the 4,5- or the 5,6-position and correspondingly $R_4$ and $R_5$ are in positions 6 and 7, or 4 and 7, respectively, of the benzodioxole skeleton, in the form of a mixture of racemates, of racemates, diastereoisomeric antipode mixture or optical antipodes, and the pharmaceutically acceptable salts of such a compound in which A represents $OR_6$ wherein $R_6$ represents hydrogen, with bases.

2. A compound of the formula I given in claim 1 in which $R_1$ represents phenyl or pyridyl each of which is unsubstituted or substituted by lower alkyl, lower alkoxy or halogen, $R_2$ represents primary lower alkyl, $R_3$ represents hydrogen or lower alkyl, $R_5$ represents hydrogen and A represents $OR_6$ wherein $R_6$ represents hydrogen or lower alkyl, and $R_4$ represents lower alkyl bonded in the 5-position of the tricyclic compound and at the same time the divalent radical in formula I is in the 4,5-position of the benzodioxole skeleton, or $R_4$ represents hydrogen and at the same time the divalent radical in formula I is in the 5,6-position of the benzodioxole skeleton, in the form of a mixture of racemates, of racemates, diastereoisomeric antipode mixtures or optical antipodes, and the pharmaceutically acceptable salts of such a compound in which A represents $OR_6$ wherein $R_6$ represents hydrogen, with bases.

3. A compound of the formula I given in claim 1 in which $R_1$ represents phenyl that is unsubstituted or substituted by lower alkyl, lower alkoxy or halogen, $R_2$ represents primary lower alkyl, each of $R_3$ and $R_5$ represents hydrogen and A represents $OR_6$ wherein $R_6$ represents hydrogen or lower alkyl, and $R_4$ represents lower alkyl bonded in the 5-position of the tricyclic compound and at the same time the divalent radical in formula I is in the 4,5-position of the benzodioxole skeleton, or $R_4$ represents hydrogen and at the same time the divalent radical in formula I is in the 5,6-position of the benzodioxole skeleton, stereoisomeric antipode mixtures or optical antipodes, and the pharmaceutically acceptable salts of such a compound in which A represents $OR_6$ wherein $R_6$ represents hydrogen, with bases.

4. A compound of the formula I given in claim 1 in which $R_1$ represents phenyl that is unsubstituted or substituted by lower alkyl, lower alkoxy or halogen, $R_2$ represents primary lower alkyl, each of $R_3$ and $R_5$ represents hydrogen and A represents $OR_6$ wherein $R_6$ represents hydrogen or lower alkyl, and $R_4$ represents methyl bonded in the 5-position of the tricyclic compound and at the same time the divalent radical in formula I is in the 4,5-position of the benzodioxole skeleton, or $R_4$ represents hydrogen and at the same time the divalent radical in formula I is in the 5,6-position of the benzodioxole skeleton, in the form of a mixture of racemates, of racemates, diastereoisomeric antipode mixtures or optical antipodes, and the pharmaceutically acceptable salts of such a compound in which A represents $OR_6$ wherein $R_6$ represents hydrogen, with bases.

5. A compound of the formula I given in claim 1 in which $R_1$ represents phenyl that is unsubstituted or substituted by lower alkyl, lower alkoxy or fluorine, $R_2$ represents methyl, each of $R_3$ and $R_5$ represents hydrogen and A represents $OR_6$ wherein $R_6$ represents hydrogen or lower alkyl, and $R_4$ represents methyl bonded in the 5-position of the tricyclic compound and at the same time the divalent radical in formula I is in the 4,5-position of the benzodioxole skeleton, or $R_4$ represents hydrogen and at the same time the divalent radical in formula I is in the 5,6-position of the benzodioxole skeleton, in the form of a mixture of racemates, of racemates, diastereoisomeric antipode mixtures or optical antipodes and the pharmaceutically acceptable salts of such a compound in which A represents $OR_6$ wherein $R_6$ represents hydrogen, with bases.

6. A compound according to claim 5 which is 7,8-dihydro-5,7-dimethyl-6-oxo-7-phenyl-6H-indeno[4,5-d]-1,3-dioxole-2-carboxylic acid in the form of a mixture of racemates, a racemate, a diastereoisomeric antipode mixture or optical antipodes, and the pharmaceutically acceptable salts thereof with bases.

7. A compound according to claim 5 which is 7,8-dihydro-5,7-dimethyl-6-oxo-7-phenyl-6H-indeno[4,5-d]-1,3-dioxole-2-carboxylic acid having a melting point of 161°–163° C., and the pharmaceutically acceptable salts thereof with bases.

8. A compound according to claim 5 which is 7,8-dihydro-5,7-dimethyl-7-(2-fluorophenyl)-6-oxo-6H-indeno[4,5-d]-1,3-dioxole-2-carboxylic acid, and the pharmaceutically acceptable salts thereof with bases.

9. A compound according to claim 5 which is 6,7-dihydro-6-methyl-5-oxo-6-phenyl-5H-indeno[4,5-d]-1,3-dioxole-2-carboxylic acid, and the pharmaceutically acceptable salts thereof with bases.

10. A compound according to claim 5 which is 6,7-dihydro-6-(4-fluorophenyl)-6-methyl-5-oxo-5H-indeno[4,5-d]-1,3-dioxole-2-carboxylic acid, and the pharmaceutically acceptable salts thereof with bases.

11. A compound according to claim 5 which is 7,8-dihydro-5,7-dimethyl-7-(4-fluorophenyl)-6-oxo-6H-indeno[4,5-d]-1,3-dioxole-2-carboxylic acid or which the sodium salt monohydrate melts at 188°–190° C., and the pharmaceutically acceptable salts thereof with bases.

12. A compound according to claim 5 which is 7,8-dihydro-5,7-dimethyl-6-oxo-7-phenyl-6H-indeno[4,5-d]-1,3-dioxole-2-carboxylic acid ethyl ester having a melting point of 96°–97° C.

13. A compound according to claim 5 which is 7,8-dihydro-5,7-dimethyl-6-oxo-7-phenyl-6H-indeno[4,5-d]-1,3-dioxole-2-carboxylic acid ethyl ester having a melting point of 93°–94° C.

14. A pharmaceutical composition having diuretic activity comprising a diuretically effective amount of a compound according to claim 1 or of a pharmaceutically acceptable salt of a compound according to claim 1 capable of salt formation, together with at least one pharmaceutical carrier.

15. A pharmaceutical composition having diuretic activity comprising a diuretically effective amount of a compound according to claim 1 or of a pharmaceutically acceptable salt of such a compound in which A represents $OR_6$ wherein $R_6$ is hydrogen, with a base, together with at least one pharmaceutical carrier.

16. A pharmaceutical composition having diuretic activity comprising a diuretically effective amount of a compound according to claim 3 or of a pharmaceutically acceptable salt of such a compound in which A represents $OR_6$ wherein $R_6$ is hydrogen, with a base, together with at least one pharmaceutical carrier.

17. A pharmaceutical composition having diuretic activity comprising a diuretically effective amount of a compound according to claim 3 or of a pharmaceutically acceptable salt of such a compound in which A represents $OR_6$ wherein $R_6$ is hydrogen, with a base, together with at least one pharmaceutical carrier.

18. A pharmaceutical composition having diuretic activity comprising a diuretically effective amount of the compound according to claim 6 or of a pharmaceutically acceptable salt thereof with a base, together with at least one pharmaceutical carrier.

19. A method for treating oedema or hypertension in a mammal comprising administering to said mammal an amount effective against oedema or hypertension of a compound according to claim 1 or of a pharmaceutically acceptable salt of a compound according to claim 1 that is capable of salt formation.

20. A method for treating oedema or hypertension in a mammal comprising administering to said mammal an amount effective against oedema or hypertension of a compound according to claim 1 or of a pharmaceutically acceptable salt of such a compound in which A represents $OR_6$ wherein $R_6$ is hydrogen, with a base.

21. A method for treating oedema or hypertension in a mammal comprising administering to said mammal an amount effective against oedema or hypertension of a compound according to claim 5 or of a pharmaceutically acceptable salt of a such a compound in which A represents $OR_6$ wherein $R_6$ is hydrogen, with a base.

22. A method for treating oedema or hypertension in a mammal comprising administering to said mammal an amount effective against oedema or hypertension of the compound according to claim 6 or of a pharmaceutically acceptable salt thereof with a base.

* * * * *